(12) United States Patent
Boland et al.

(10) Patent No.: US 7,469,440 B2
(45) Date of Patent: Dec. 30, 2008

(54) ELECTRIC TOOTHBRUSH

(75) Inventors: Bernhard Boland, Frankfurt am Main (DE); Christian Junk, Eschborn (DE)

(73) Assignee: Braun GmbH, Kronberg (DE)

( * ) Notice: Subject to any disclaimer, the term of this patent is extended or adjusted under 35 U.S.C. 154(b) by 592 days.

(21) Appl. No.: 10/537,022

(22) PCT Filed: Aug. 1, 2003

(86) PCT No.: PCT/EP03/08518

§ 371 (c)(1), (2), (4) Date: May 31, 2005

(87) PCT Pub. No.: WO2004/049968

PCT Pub. Date: Jun. 17, 2004

(65) Prior Publication Data

US 2006/0021165 A1   Feb. 2, 2006

(30) Foreign Application Priority Data

Nov. 28, 2002   (DE) ................ 102 55 390

(51) Int. Cl.
A61C 17/36   (2006.01)
(52) U.S. Cl. .............. 15/22.1; 15/22.2; 15/29
(58) Field of Classification Search ........... 15/22.1, 15/22.2, 29, 23, 22.428
See application file for complete search history.

(56) References Cited

U.S. PATENT DOCUMENTS

| 3,178,754 | A | | 4/1965 | Cleverdon | |
| 4,603,448 | A | * | 8/1986 | Middleton et al. | 15/22.1 |
| 4,710,995 | A | * | 12/1987 | Joyashiki et al. | 15/22.1 |
| 5,974,613 | A | * | 11/1999 | Herzog | 15/22.1 |
| 6,766,549 | B2 | * | 7/2004 | Klupt | 15/22.2 |
| 6,836,918 | B1 | * | 1/2005 | Wong | 15/22.1 |
| 2002/0035761 | A1 | * | 3/2002 | Fritsch et al. | 15/22.1 |
| 2002/0152565 | A1 | * | 10/2002 | Klupt | 15/29 |

FOREIGN PATENT DOCUMENTS

| DE | 2 019 003 | 11/1971 |
| DE | 85 35 385.2 | 5/1986 |
| DE | 199 35 067 | 2/2001 |

* cited by examiner

*Primary Examiner*—Lee D Wilson
(74) *Attorney, Agent, or Firm*—Fish & Richardson P.C.

(57) ABSTRACT

An electric toothbrush including a pressure fluid device for applying fluid under pressure to teeth to be cleaned or to a bristle set. The pressure fluid device includes a pressure fluid supply in the interior of a movable drive translator. A brush part with a carrier tube is movably mounted with a drive translator therein adapted to be coupled to a drive element in a handle part. A movably mounted bristle carrier mounts a set of bristles and is adapted to be driven in an oscillatory manner by the drive translator. A motor in the handle part drives a drive element adapted to be coupled to a drive element in the brush part and with a pressure fluid conveying device driven by the motor. A pressure fluid channel, which directs the pressure fluid to the toothbrush head, is integrated into the drive translator.

18 Claims, 4 Drawing Sheets

ELECTRIC TOOTHBRUSH

The present invention relates to electric toothbrushes, and more particularly, to electric toothbrushes that deliver fluid under pressure to teeth to be cleaned or to a bristle set.

BACKGROUND

Toothbrushes have been proposed in which pressurized-air nozzles are provided adjacent to the bristles in order to cleanse teeth and interproximal spaces with pressurized air. In addition to the cleaning action of the bristles, the pressurized air blows away adhering particles and produces a massage effect. U.S. Pat. No. 3,823,710 discloses a handheld toothbrush in which a pulsed stream of air is discharged from a tip element arranged at the forward end adjacent to the bristle set, said stream of air being produced by a tandem diaphragm pump. The tip element is connected with a pressurized air channel in the neck of the toothbrush which is connected to the air pump at the handle part through a tube. U.S. Pat. No. 3,178,754 proposes an electric toothbrush with a compressed-air device. Provided in the handle part of the toothbrush is an air pump which directs compressed air into the interior of the moving toothbrush head. Formed underneath the bristle carrier is a pressure fluid chamber in which the pulsing air pressure arriving from the piston pump develops into a uniform stream, exiting to the bristle set through outlet nozzles as a substantially uniform flow of air.

Patent DE 20 19 003 A1 discloses an electric toothbrush where the brush head impinges a jet of water on the teeth to be cleaned or the surrounding gums. The water jet device comprises a compressor driven by the drive motor of the toothbrush and conveying pressurized air into a water reservoir in the handle of the toothbrush, thereby providing a pressurized water-and-air mixture. This mixture is directed through a line into a feed channel in the interior of the brush attachment from which it is fed to the brush head. In contrast to modern brush attachments, this known brush attachment is moved overall, that is, it has no brush tube which is adapted to be fixedly coupled to the handle and would have in its interior a separate drive train and at its forward end a movably mounted bristle carrier.

SUMMARY

The aforementioned problems are overcome by the present disclosure of an electric toothbrush including a brush part having a pressure fluid device for applying fluid under pressure to the teeth to be cleaned or to the bristle set. The pressure fluid device comprises a pressure fluid supply in the interior of the movable drive translator. A pressure fluid channel, which directs the pressure fluid to the toothbrush head, is hence integrated into the typically rod- or bar-shaped drive translator.

In a preferred embodiment, the drive translator is constructed as a hollow shaft mounted in the carrier tube for rotation about its longitudinal axis having a coupling member at an end close to the handle part for coupling a drive element of the handle portion. The coupling member comprises a fluid coupling through which the fluid channel in the interior of the hollow shaft is connectible with a fluid channel in the interior of the drive shaft element of the handle part. The oscillatory rotary drive movement of the drive shaft in the carrier tube may be converted into the drive movement of the bristle carrier in a variety of ways. In one embodiment, an eccentric coupling member is fastened to the drive shaft in a manner preventing relative rotation, where the eccentric coupling member is engaged with the bristle carrier in order to drive the latter in a rotary oscillatory manner. The motion axis of the bristle carrier and the motion axis of the drive shaft extend in directions essentially normal to each other.

In yet another embodiment, the driving motion of the drive translator in the carrier tube is along a single axis only, thereby facilitating the passing-on of the fluid stream which exits from the end of the drive translator close to the brush head. The fluid stream is introduced into a fluid channel in the carrier tube wall in the area of the bearing carrying the drive translator for rotation about its longitudinal axis. Hence, the fluid line in the carrier tube wall is in fluid communication with the bearing section for the drive translator. With its other end, the pressure fluid channel in the carrier tube wall is in fluid communication with the movably mounted bristle carrier. To simplify the introduction of the pressure fluid from the pressure fluid channel in the carrier tube wall into the bristle carrier, the pressure fluid channel is routed from the carrier tube wall into the bearing section in which the bristle carrier is rotatably mounted. In a preferred embodiment, the bristle carrier may sit on a bearing pin secured in a head section of the brush carrier tube. The fluid channel passes preferably through the bearing pin of the bristle carrier. A hollow pivot pin for the bristle carrier is provided, through which the pressure fluid can be supplied to the bristle carrier. Extending through the interior of the bristle carrier is then likewise at least one pressure fluid channel which is routed to a pressure fluid outlet orifice at the base of the bristle carrier in which the bristles are anchored. Conveniently, the bristle carrier provides a central discharge nozzle which is constructed such that a pressure fluid jet is discharged from the bristle carrier roughly parallel to the bristle main direction and directed against the teeth to be cleaned.

The pressure fluid supply in the interior of the brush part, in a preferred embodiment, dispenses with separate flexible tubes and is formed exclusively in the interior of functional components of the brush part that already exist for the performance of other functions. The pressure fluid channels run in components as, for example, the movable drive train in the interior of the carrier tube, all of which accordingly fulfill a dual function. Because separate flexible tubes and the like are dispensed with, a highly compact construction of the brush part can be accomplished.

The handle part of the electric toothbrush, in a preferred embodiment, has a compact structure. The pressure fluid conveying device is seated between the motor and the gear step and is driven, together with the gear step, by a common drive element. Hence, no separate gear step for the pressure fluid conveying device is provided. The pressure fluid conveying device transmits the drive motion of the motor to the gear step which generates the movement of the drive translator in the interior of the carrier tube of the brush section, meaning that the drive motion of the motor is transmitted through the pressure fluid conveying device to the gear step. Additional losses, which would be produced by a further gear step, are avoided. Furthermore, comparatively short pressure fluid lines can find application, which in the known arrangement of the pressure fluid conveying device on the motor side remote from the brush part are substantially longer.

The compact arrangement is, however, not at the expense of the pressure fluid conveying device being integrated into the housing of the handle part or being formed integrally by parts of the drive train. In a further embodiment, the pressure fluid conveying device is a separate assembly in its own right, which is arranged in the interior of the handle part. Preferably, the pressure fluid conveying device is an air pump, in which the pressure fluid discharge is preferably only air, that is, no water is added and no water jet is discharged. The pressure fluid channels form air channels.

In yet another embodiment, the pressure fluid conveying device is seated on an eccentric element connected to the motor shaft and carries a coaxial eccentric element for driving the gear step. Accordingly, the pressure fluid conveying device may sit on the same eccentric element that drives the gear step which generates the drive motion for the drive translator in the carrier tube of the brush part.

The drive element extending out of the housing of the handle part and driven in an oscillatory manner is utilized, in a preferred embodiment, for passing on the pressure fluid stream generated by the pump, where the drive element is adapted to be coupled to the drive translator in the carrier tube of the brush part. The drive element, drivable in oscillatory manner in the handle part, may have in its interior a pressure fluid channel which communicates with the pressure fluid conveying device. Preferably, the drive element is constructed as a rotatably mounted hollow shaft having at its end protruding from the handle part a coupling member for coupling to the drive translator in the brush part, with the coupling member comprising a fluid coupling allowing the pressure fluid to be directed into the interior of the drive translator in the brush part.

In an embodiment where the construction of the two drive elements includes coupled hollow shafts and the pressure fluid passes directly from oscillatory drive element to oscillatory drive element, it is possible to construct the coupling of the carrier tube of the brush part to the handle part in a simple manner. The connector on the handle part housing can be free from a pressure fluid coupling for releasably fastening the carrier tube of a brush part. Both the drive coupling and the pressure fluid coupling are provided on the movable drive elements provided in the interior of the brush tube and typically fabricated from metal.

The hollow shaft mounted in the handle part and driven by the gear step may be connected to the pressure fluid conveying device in a variety of ways. To compensate for the movement of the drive element driven to oscillate and protruding from the handle part housing, the connection may be implemented in the form of a flexible tube connectible to the pressure outlet of the pressure fluid conveying device at its one end and to the drive element moved in an oscillatory pattern at its other end. In a preferred embodiment, provision can be made for the flexible tube to be connected to a connecting rod which drives the hollow shaft in the handle part and has in its interior a pressure fluid channel communicating with the pressure fluid channel in the interior of the hollow shaft. Preferably, the pressure conveying device constructed as a pump is arranged such that its pressure outlet lies at the end facing the brush head. This makes it possible to provide a short length of flexible tubing.

Further objects, advantages, features and application possibilities of the present invention will become apparent from the subsequent description of a preferred embodiment with reference to the accompanying drawings.

DETAILED DESCRIPTION

Figure 1:
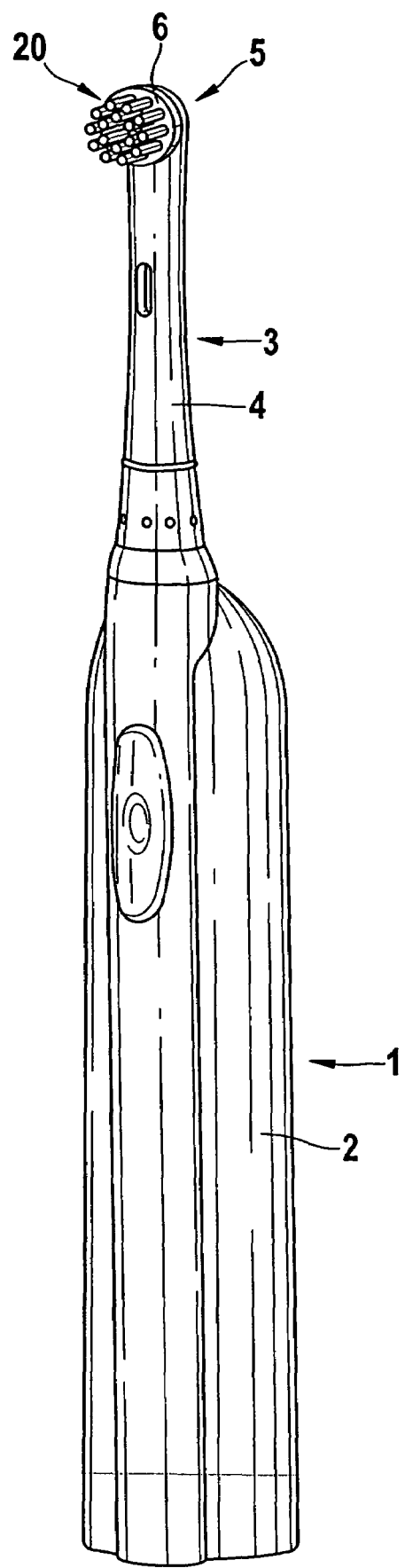
FIG. 1 is a perspective view of an electric toothbrush having a handle part and, seated thereon, a brush part with a bristle carrier adapted to be driven in rotary oscillatory manner in accordance with a preferred embodiment of the invention.

The toothbrush shown in FIG. 1 comprises a handle part 1 with an essentially cylindrical handle part housing 2 and a brush part 3 with an essentially cylindrical carrier tube 4 mounting at its head section 5 a bristle carrier 6 for rotation about an axis of rotation 21 transverse to the longitudinal direction of the toothbrush. The brush part 3 is releasably connected to the handle part 1, so that the brush part 3 can be replaced when worn.

Figure 2:
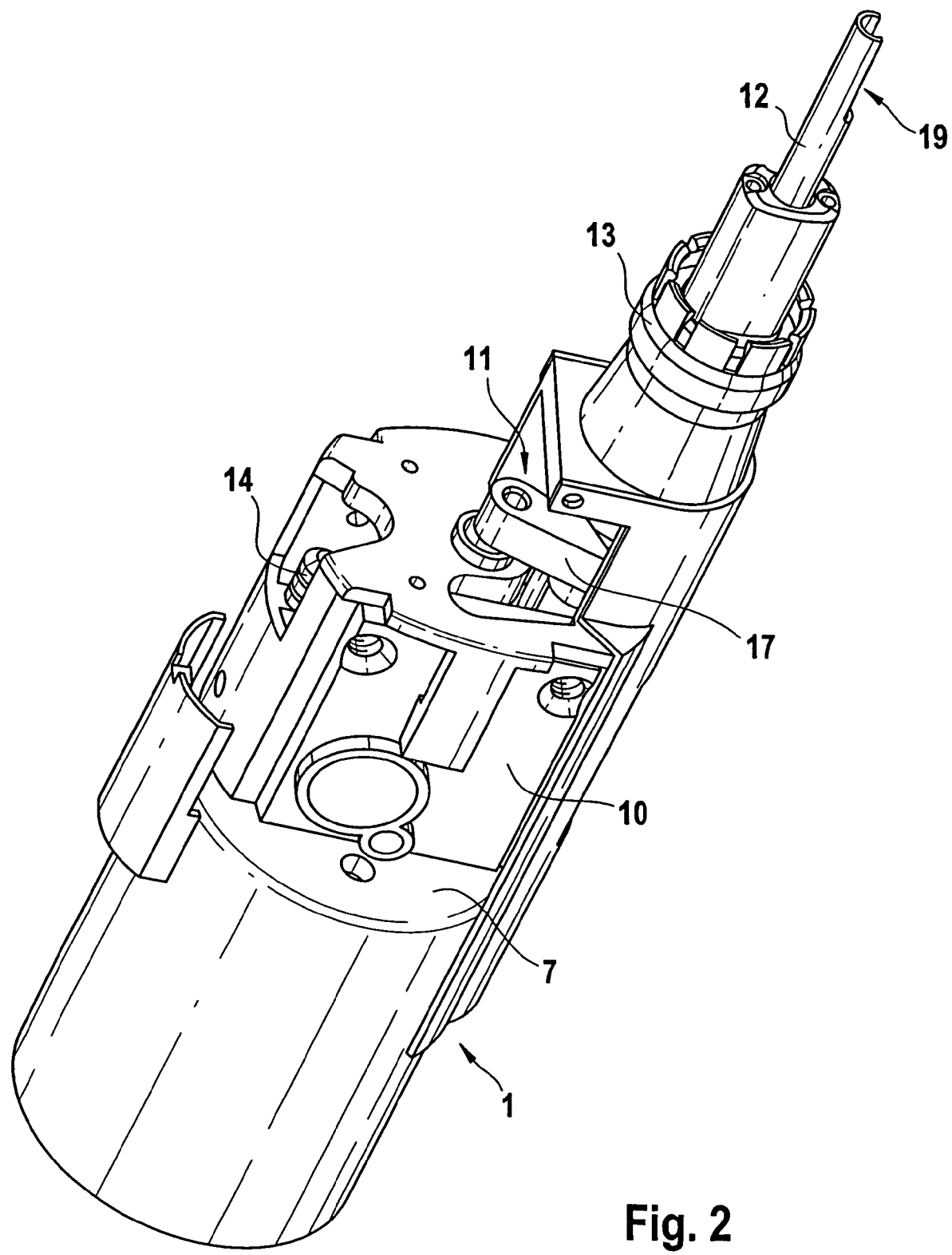
FIG. 2 is a perspective view of the interior of the handle part, with the handle part housing cut away to expose the arrangement of a pressure fluid pump and the gear step for generating the drive motion.
Figure 4:
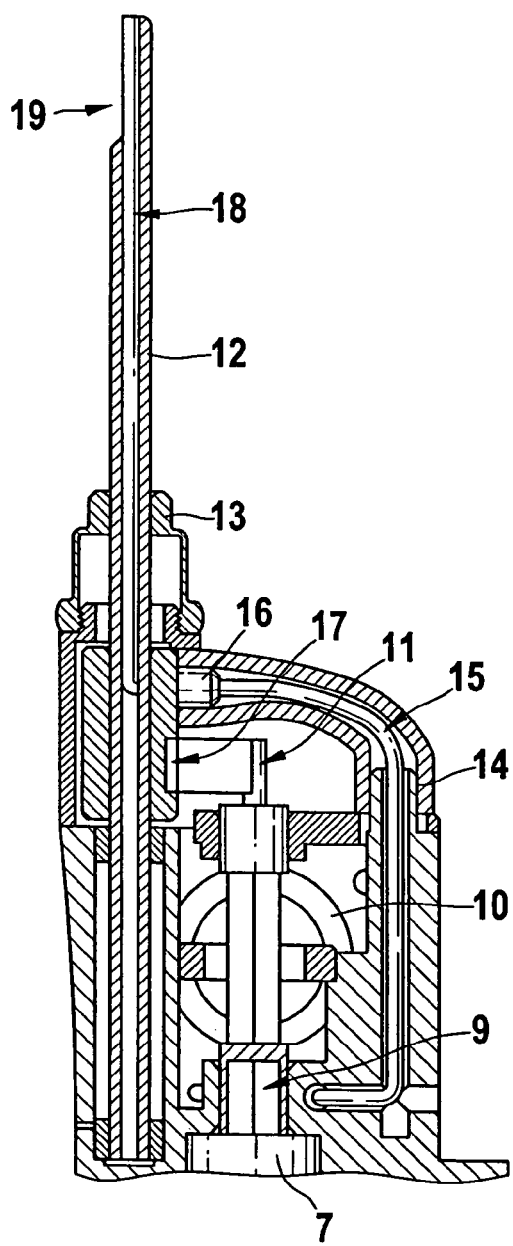
FIG. 4 is a schematic sectional view of the pump provided in the handle part and its connection to a pressure fluid channel in the interior of a drive element driven to oscillate in the handle part, which drive element is coupled to a drive translator in the brush part.

Arranged in the interior of the handle part housing 2, which is omitted in FIGS. 2 and 4, is an electric motor 7 having a motor shaft 8 on which a non-circular drive element 9 is seated in a manner preventing relative rotation. Seated on the non-circular drive element 9 is an air pump 10 which is arranged in front of the electric motor 7 in axial direction and is driven by the drive element 9. The same drive element 9 or a drive element 9 coaxially connected therewith extends through the air pump 10, protruding therefrom with its forward end. Connected to the forward end of the drive element 9 is a gear step 11 in the form of a four-bar linkage, which transmits the drive motion of the drive element 9 to a drive shaft 12 arranged parallel and in offset relation to the motor shaft 8. The gear step 11 is constructed such that the drive shaft 12 is driven to oscillate in a rotary pattern about its longitudinal axis. With its forward end the drive shaft 12 protrudes from the handle part housing 2 which in the exit area of the drive shaft 12 is constructed to fit around the drive shaft, forming a connector 13 for the carrier tube 4 of the brush part 3.

The air pump 10 which is driven by the motor 7 via the drive element or the eccentric element 9 has a pressure fluid outlet 14 at the end close to the brush part 3, which outlet is connected to a pressure fluid line 15 in the form of a flexible tube. The pressure fluid line 15 connects the pressure fluid outlet 14 of the air pump 10 with a pressure fluid channel 16 formed in a connecting rod 17 that drives the drive shaft 12. The pressure fluid channel 16, which is constructed as a flexible tube, is sufficiently flexible to be able to compensate for the movement of the drive shaft 12. The pressure fluid channel 16 in the connecting rod 17 is in fluid communication with a pressure fluid channel 18 in the interior of the drive shaft 12 which is constructed as a hollow shaft. The pressure fluid channel 18 has its outlet at the free end of the drive shaft that extends out of the handle part 1 where a coupling member 19 or coupling section is provided for coupling the drive shaft 12 to a drive translator in the interior of the carrier tube 4 of the brush part 3.

Figure 5:
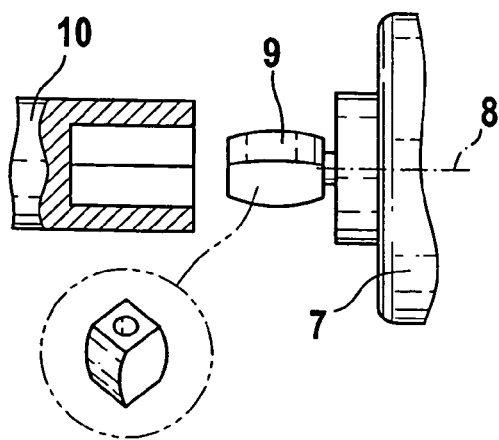
FIG. 5 is a schematic part sectional view of the coupling between the pump and the eccentric element of the motor for driving the toothbrush.

As FIG. 5 shows, there is no rigid, that is, completely immovable connection provided between the drive element 9 and the air pump 10. Rather, the connection is of such flexibility that an angular offset between the drive element 9 and the air pump 10 or the connection of the gear step 11 can be compensated for. To this effect, the drive element 9 is not completely straight but has in longitudinal direction slightly barreled flanks which enable the air pump 10 to tilt somewhat in a direction transverse to the longitudinal axis to balance an angular offset. The air pump 10 sits directly on the polygonal connector 13, the air pump has no bearing of its own at the motor end, any bearing being formed directly by the drive element 9.

Figure 3:
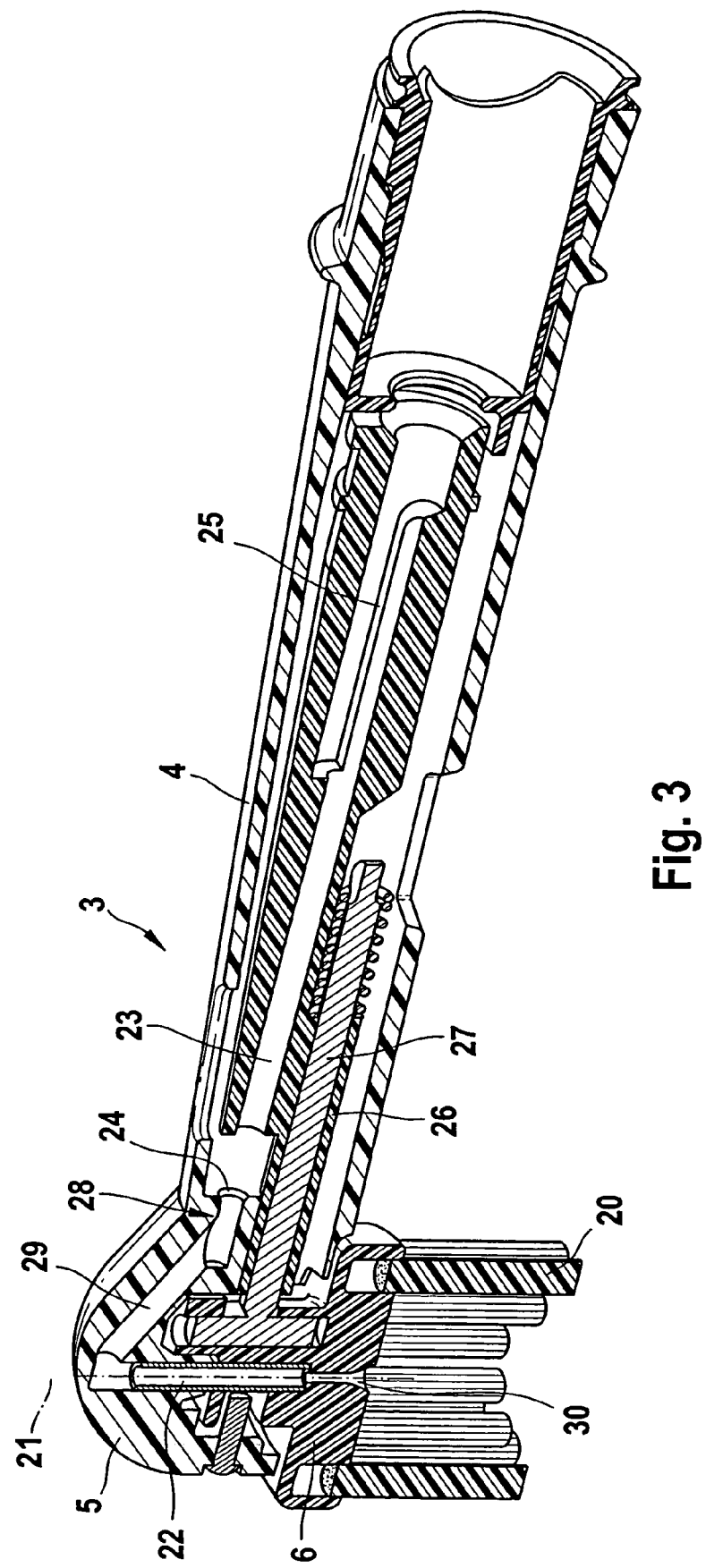
FIG. 3 is a perspective sectional view of the brush part of FIG. 1, showing the path of the pressure fluid supply to the driven bristle carrier through the drive train.

The brush part 3 is equipped with an approximately circular bristle set 20 mounted on the disk- or plate-shaped bristle carrier 6. As FIG. 3 shows, the bristle carrier 6 is mounted on the head section 5 of the carrier tube 4 for rotation about an axis of rotation 21 essentially normal to the longitudinal axis of the toothbrush. The axis of rotation 21 is defined by a bearing pin 22 received in a corresponding bore in the head section 5 of the brush part 3. The bristle carrier 6 has a corresponding bore with which it sits on the bearing pin 22.

To transmit the drive motion of the drive shaft 12 in the handle part to the bristle carrier 6, the carrier tube 4 mounts in its interior a drive translator 23 constructed as a drive shaft that is mounted for rotation about its longitudinal axis. With its end close to the head section the drive shaft sits in a bearing bore 24 formed in the body of the brush part 3. With its end close to the handle part the drive shaft 23 can be locked with the drive shaft 12 of the handle part in a manner preventing relative rotation. The two drive shafts 12 and 23 have complementary coupling sections 19 and 25 engageable with each other in a non-rotating relationship. In this arrangement the coupling sections 25 also form a fluid coupling to direct the air stream exiting from the drive shaft 12 of the handle part into the interior of the drive shaft 23 which is likewise constructed as a hollow shaft. Hence the interior of the drive shaft 23 forms likewise a pressure fluid channel.

At its end close to the brush head the drive shaft 23 carries non-rotatably an eccentric element 26 receiving in it rotatably a translator pin 27 that extends essentially parallel to the drive shaft 23. With its forward end the translator pin 27 makes engagement with a longitudinal recess in the bristle carrier 6, which recess extends parallel to the axis of rotation 21. Through the translator pin 27 the oscillatory rotational drive motion of the drive shaft 23 is converted into a likewise oscillatory rotational motion of the bristle carrier 6.

The pressure fluid channel in the interior of the drive shaft 23 has its outlet in the bearing section 28 around the bearing bore 24. The bearing section 28 is formed by the material of the carrier tube 4 or the head section 5 of the brush part 3. Adjoining in the wall of the head section 5 is a pressure fluid channel 29 which communicates with the bearing section 28 or the outlet of the pressure fluid channel in the drive shaft 23. The pressure fluid channel 29 opens into the bore for the bearing pin 22 which, constructed as a hollow pin, is formed as continuation of the pressure fluid channel 29. Extending through the bristle carrier 6, the pressure fluid channel finally ends on the surface of the bristle carrier 6 in which the bristle set 20 is anchored. As FIG. 3 shows, the corresponding passage opening for the pressurized air extends approximately centrally all the way through the bristle carrier. The outlet orifice 30 is constructed as a nozzle so that a high-velocity free jet exits between the bristles and impinges on the teeth. Of course it would also be possible to provide a plurality of outlet orifices. In this event provision could be made in the bristle carrier 6 for a distributor chamber which is supplied with pressurized air from the channel in the rotary pin 21 and distributes it to plural outlet orifices. Preferable is however the previously described central outlet orifice.

To guarantee a sufficient level of hygiene, in one embodiment, the toothbrush may be provided with an inlet-air filter in the base of the handle part 1 so that only filtered air can be discharged.

The invention claimed is:

1. A brush part for an electric toothbrush, the brush part comprising
    a carrier tube;
    a drive translator movably mounted within the carrier tube and couplable to a drive in an electric toothbrush handle part; and
    a bristle carrier movably mounted to the carrier tube and carrying a set of bristles, the bristle carrier drivable in an oscillatory manner by the drive translator;
    wherein the drive translator defines an interior fluid supply channel forming part of a fluid path providing fluid communication to the bristle set.

2. The brush part according to claim 1 wherein the drive translator is constructed as a hollow shaft mounted in the carrier tube for rotation about a longitudinal axis of the drive translator, and having at an end thereof a coupling member configured to couple the drive translator to a drive element of the handle part, said coupling member comprising a fluid coupling through which the fluid channel of the drive translator is connectible with a fluid channel in the interior of the drive element of the handle part.

3. The brush part according to claim 1 wherein the fluid supply channel of the drive translator provides fluid communication to a pressure fluid outlet orifice defined in the movable bristle carrier, said orifice communicating with a pressure fluid supply channel defined in a bearing pin of the bristle carrier.

4. The brush part according to claim 3 wherein the pressure fluid outlet orifice defined in the movable bristle carrier is located in the bristle set.

5. The brush part according to claim 1 wherein the carrier tube defines a pressure fluid supply channel connecting fluid supply channel of the drive translator with a pressure fluid channel defined in the bristle carrier.

6. The brush part according to claim 5 wherein the pressure fluid channel defined in the bristle carrier has first and second ends, the first end terminating in a bearing section for carrying the drive translator and the second end terminating in a bearing section for carrying the bristle carrier.

7. The brush part according to claim 1 wherein the path providing fluid communication to the bristle carrier is free of flexible tubes and is formed exclusively in components of the brush part that serve other functions in addition to providing hydraulic communication.

8. The brush part according to claim 1 further comprising a pivot pin defining a hollow core and rotatably mounting the bristle carrier on the carrier tube.

9. A handle part of an electric toothbrush configured to drive a removable brush part, the handle part comprising:
    a handle part housing;
    a motor having a motor shaft and disposed within the handle part housing;
    a drive element operably connected to the motor shaft through a gear step and positioned to drive an associated removable brush part; and
    pump driven by the motor shaft and defining a fluid outlet;
    wherein both the pump and the gear step are driven by a driver connected to the motor drive shaft, the pump being disposed between the motor and the gear step; and
    wherein the drive element defines a pressure fluid channel in fluid communication with the pump.

10. The handle part according to claim 9, comprising
a first eccentric element connected to the motor shaft, wherein the pump is seated On the eccentric element; and
a second eccentric element located on the pump for driving the gear step.

11. The handle part according to claim 9 wherein the pump is an air pump.

12. The handle part according to claim 9, comprising
a flexible tube connecting the drive element to the fluid outlet of the pump; and
a connecting rod that drives the drive element, wherein the connecting rod is in fluid communication with the flexible tube.

13. The handle part according to claim 9 wherein the pump comprises a pump casing separate from the handle part housing.

14. The handle part according to claim 9 wherein the handle part housing comprises a connector for the releasable fastening of a carrier tube of the brush part, said connector being free from a drive coupling and free from a pressure fluid coupling.

15. The handle part of claim 9 wherein the motor drives the drive element in an oscillatory manner.

16. The handle part of claim 9 wherein the gear step comprises a four-bar linkage.

17. The handle part of claim 9 wherein the pressure fluid channel is defined in a rotatably mounted hollow shaft.

18. A replacement brush head for an electric toothbrush handle, the brush head comprising
a carrier tube;
a drive translator movable within the carrier tube and having a first end operably couplable to a drive of an electric toothbrush handle;
a bristle carrier movably mounted on the carrier tube and carrying a set of bristles, the bristle carrier operably connected to, and drivable in oscillatory manner by, the drive translator;
wherein the drive translator defines a passage therein, the passage forming a part of a fluid supply channel providing fluid communication between the first end of the drive translator and the bristle carrier, such that fluid pumped into the drive translator from the electric toothbrush handle is delivered to the bristle carrier.

* * * * *

UNITED STATES PATENT AND TRADEMARK OFFICE
CERTIFICATE OF CORRECTION

PATENT NO. : 7,469,440 B2
APPLICATION NO. : 10/537022
DATED : December 30, 2008
INVENTOR(S) : Bernhard Boland and Christian Junk It is certified that error appears in the above-identified patent and that said Letters Patent is hereby corrected as shown below:

Column 7, Claim 10, Line 2;

Delete "clement" and Insert --element--

Signed and Sealed this

Third Day of March, 2009

JOHN DOLL
*Acting Director of the United States Patent and Trademark Office*